US006260005B1

(12) United States Patent
Yang et al.

(10) Patent No.: US 6,260,005 B1
(45) Date of Patent: Jul. 10, 2001

(54) FALCON: AUTOMATED OPTIMIZATION METHOD FOR ARBITRARY ASSESSMENT CRITERIA

(75) Inventors: Tser-Yuan Yang; Edward I. Moses; Christine Hartmann-Siantar, all of Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/247,653

(22) Filed: Feb. 9, 1999

Related U.S. Application Data (63) Continuation-in-part of application No. 08/610,917, filed on Mar. 5, 1996, now Pat. No. 5,870,697.
(60) Provisional application No. 60/100,056, filed on Sep. 10, 1998.
(51) Int. Cl.[7] ............... G06F 7/60; G06F 17/10; G06F 7/48; G06F 7/56
(52) U.S. Cl. ................... 703/11; 703/2; 703/5; 703/6
(58) Field of Search ................ 600/1; 703/2, 5, 703/6, 11

(56) References Cited

U.S. PATENT DOCUMENTS

| | | | |
|---|---|---|---|
| 5,027,818 | * | 7/1991 | Bova et al. ............... 128/653 |
| 5,291,404 | * | 3/1994 | Kurokawa et al. ........ 600/1 |
| 5,341,292 | * | 8/1994 | Zamenhof ............... 600/425 |

OTHER PUBLICATIONS

Solberg; "Implications of tissue heterogeneity for radiosurgery in head and neck tumors"; Int. J. Radiation Oncology Biology Physics; vol. 32; pp. 235–239, Apr. 1995.*

Morrill; "Conventional treatment planning optimization using simulated annealing"; Int. J. Radiation Oncology Biology Physics; vol. 32; pp. 298, 1995.*

Williamson; "The Sievert integral revisited: evaluation and extension to low energy brachytherapy", Int. J. Radiation Oncology Biology Physics; vol. 32; pp. 200, 1995.*

* cited by examiner

*Primary Examiner*—Kevin J. Teska
*Assistant Examiner*—Hugh Jones
(74) *Attorney, Agent, or Firm*—John P. Woolridge; Alan H. Thompson (57) ABSTRACT

FALCON is a method for automatic multivariable optimization for arbitrary assessment criteria that can be applied to numerous fields where outcome simulation is combined with optimization and assessment criteria. A specific implementation of FALCON is for automatic radiation therapy treatment planning. In this application, FALCON implements dose calculations into the planning process and optimizes available beam delivery modifier parameters to determine the treatment plan that best meets clinical decision-making criteria. FALCON is described in the context of the optimization of external-beam radiation therapy and intensity modulated radiation therapy (IMRT), but the concepts could also be applied to internal (brachytherapy) radiotherapy. The radiation beams could consist of photons or any charged or uncharged particles. The concept of optimizing source distributions can be applied to complex radiography (e.g. flash x-ray or proton) to improve the imaging capabilities of facilities proposed for science-based stockpile stewardship.

17 Claims, 7 Drawing Sheets

FALCON: AUTOMATED OPTIMIZATION METHOD FOR ARBITRARY ASSESSMENT CRITERIA

This application is a continuation-in-part of U.S. patent application Ser. No. 08/610,917 titled filed Mar. 5, 1996, now U.S. Pat. No. 5,870,697, and claims benefit of provisional No. 60/100,056 filed Sep. 10, 1998: "Calculation of Radiation Therapy Dose Using All Particle Monte Carlo Transport."

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to systems and methods for obtaining optimized radiation dose deposition, and more particularly for automatically generating individually optimized treatment strategies for multiple treatment goals on a single patient, multiple patients or treatment sites.

2. Description of Related Art

The goal of radiation therapy is to deliver a high, curative dose to a tumor, while minimizing the dose to normal tissues and limiting the dose in critical healthy structures to their radiation dose tolerance. In the past several years, significant advances have been made to identify and characterize in three dimensions the patient's tumor, as well as normal, sensitive structures, and then deliver a high dose that conforms to the three-dimensional volume of the tumor. Enabling imaging technologies are computed tomography (CT) and magnetic resonance imaging (MRI) scans of the body, which are now a common part of radiation therapy planning. New methods for specifically identifying the location of tumors and cancerous tissue include magnetic resonance spectroscopy (MRS) and proton emission spectroscopy (PET). In addition, computer-controlled beam modifiers, such as multileaf collimators and dynamic wedges on linear accelerators offer the ability to both shape the radiation beam and sculpt the beam profile in three dimensions. Sculpting the beam profile is accomplished using a technique referred to as intensity modulated radiation therapy (IMRT). Incorporated in multiple-beam plans, IMRT can deliver a complex map of dose, in which the therapy can be made to conform closely to the patient's tumor.

Two critical links required for accurate delivery of the optimal conformal therapy plan are the ability to accurately predict the dose distribution in the patient (given a dose-delivery configuration), and the ability to optimize the treatment plan or dose delivery configuration to yield the most advantageous dose distribution for the patient. The PEREGRINE dose calculation system, developed at Lawrence Livermore National Laboratory, uses Monte Carlo transport calculations to provide highly accurate three-dimensional dose calculation for radiation therapy. The FALCON automated planning system, described here, uses these accurate dose calculations to identify and prescribe the treatment plan that best meets the planners treatment objectives.

SUMMARY OF THE INVENTION

It is an object of the present invention to provide an automated radiation therapy dose planning system that uses the dose calculations from any arbitrarily accurate dose calculation system, including PEREGRINE, to identify the treatment plan that best meets the planners treatment objectives.

FALCON enables identification of the most optimized treatment configuration for multiple treatment goals simultaneously. More generally the methods described here will provide the optimized configuration with accuracy limited by the accuracy of the dose calculation algorithm and can be used for highly accurate algorithms including Monte Carlo techniques.

The FALCON system provides an automated radiation therapy dose planning system that uses the accurate dose calculations from the PEREGRINE dose calculation system or other dose calculation methods to identify the treatment plan that best meets the planners treatment objectives, thus providing a method for automatic multivariable optimization for arbitrary assessment criteria. The PEREGRINE dose calculation system is described in U.S. Pat No. 5,870,697 titled: "Calculation of Radiation Therapy Dose Using All Particle Monte Carlo Transport" which is incorporated herein by reference. FALCON can be applied to numerous fields where outcome simulation is combined with optimization and assessment criteria. A specific embodiment of FALCON is for automatic radiation therapy treatment planning. FALCON implements dose calculations into the planning process and optimizes available beam delivery modifier parameters to determine the treatment plan that best meets clinical decision-making criteria. FALCON is herein described in the context of the optimization of external-beam radiation therapy and intensity modulated radiation therapy (IMRT), but the concepts are also applicable to internal (brachytherapy) radiotherapy. The radiation beams that are usable in the present invention include photons or any charged or uncharged particles.

In the radiation therapy implementation, the method divides the problem into the following four discrete steps.
1. Case setup.
2. Beamlet dose calculation.
3. Beamlet weight optimization.
4. Plan assessment.

This method decouples the time-consuming processes of dose calculation, optimization and assessment, and rapidly optimizes the treatment plan for any arbitrary assessment criteria.

DETAILED DESCRIPTION OF THE INVENTION

Figure 1:
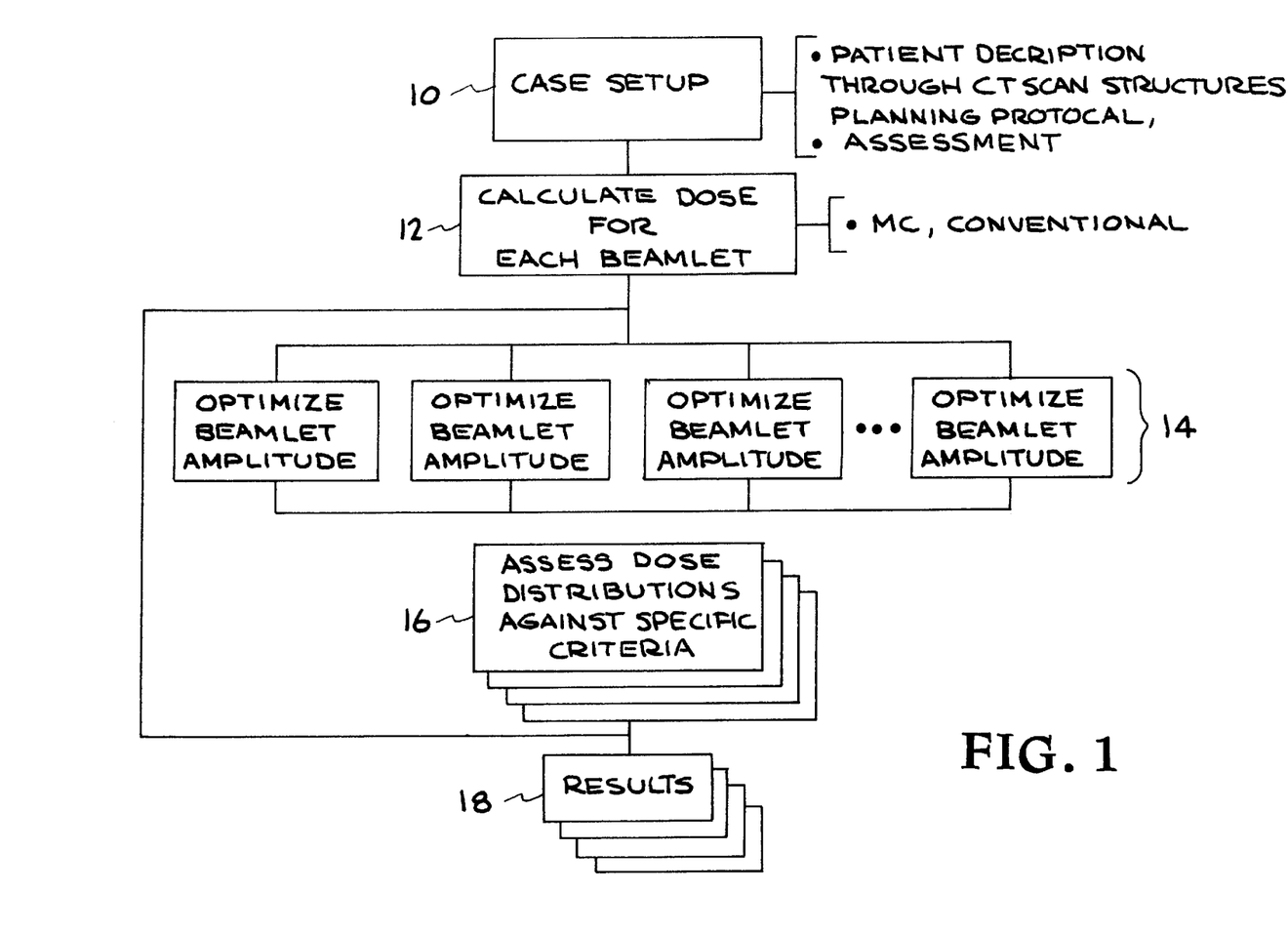
FIG. 1 is a flow chart describing the automatic treatment planning process of the present invention.

FIG. 1 shows a schematic diagram that describes FALCON's automatic treatment planning process. The following sections describe each major step in the method, and give an example that shows FALCON in operation.

In the Case Setup step (10), the user provides information concerning patient description, beam description, penalty function and assessment criteria. The patient description includes a three-dimensional map that adequately describes the patient's anatomy suitable for radiation dose calculations. The description also includes tumor/sensitive structure identification to be used in the decision-making criteria for the automatic planning process. Beam description also specifies the character (energy, particle type, delivery device) and orientation of each radiation beam. Any number of radiation sources can be used. The penalty function is a mathematical function for optimization of beamlet intensities. Assessment criteria is used for final plan assessment. The assessment criteria can be based on a variety of concepts, including (i) dose-volume analysis which optimizes the relative amount of dose in target and other sensitive structure volumes and/or optimizes the volume of the target/sensitive structure receiving greater or less than a specified dose and (ii) biological response which optimizes the probability of controlling the tumor and/or sparing sensitive structures (e.g. spinal cord, salivary glands, rectum, bladder, etc.) based on biological models of how the tumor and other tissues respond to radiation, or other methods that can describe dose or treatment goals mathematically.

Figure 2:
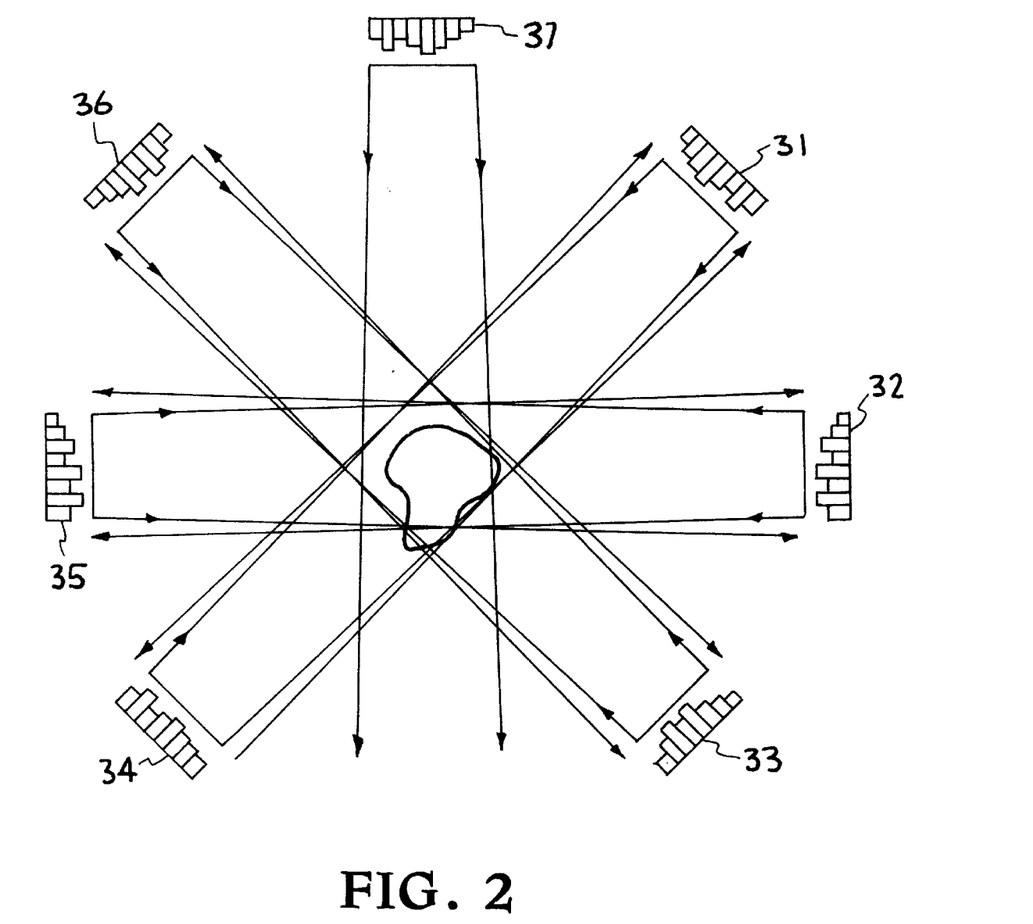
FIG. 2 shows a possible IMRT treatment configuration for a prostate cancer case.

In the Beamlet Dose Calculation step (12), FALCON divides each beam into individual beamlets. Beamlets are arbitrarily shaped sub-beams that tile the treatment beam, and are defined by masks oriented perpendicular to the central ray of each beam. The only radiation allowed through is that associated with the specific beamlet being simulated. FALCON can then use any dose calculation algorithm to determine the dose distribution in the patient for each beamlet. An example of a dose calculation algorithm that could be used is the PEREGRINE Monte Carlo dose calculation system as described in the incorporated Patent Application. FIG. 2 illustrates how each beam is broken down into beamlets (in this case for a prostate cancer treatment). The CT slice of this prostate is shown to be irradiated by seven beams. Each treatment beam is broken down into beamlets with customized intensity, as illustrated by the small histograms 31–37.

The absolute dose distribution per monitor intensity unit for each beamlet is stored (possibly in compressed form) to be used during the beamlet optimization phase.

Referring again to FIG. 1, during the beamlet optimization phase (14), FALCON determines the intensity-weight of each beamlet by optimizing according to a penalty function. As an example of one embodiment, FALCON uses a quadratic, least-squares-type penalty function, P. The form of this function would be $$P(a_1 \ldots a_n) = \int F \bullet [T-D]^2 \, dV$$

where F is the "desirability factor" (initialized to 1), T is the target dose, D is the calculated dose and ($a_1 \ldots a_n$) are the intensities of the beamlets to be determined in the optimization process. D can also be expressed as the sum of the doses contributed by each beamlet, as in the formula: $D = \Sigma a_i D_i$, where $a_i$ is the beamlet amplitude and $D_i$ is the dose per unit amplitude of the ith beamlet. F, T and D are all functions of position in the volume. The advantage of this convex, quadratic penalty function is that it has a single minimum for this constrained optimization problem ($a_i$ is greater than or equal to 0) that can be reached rapidly using quadratic programming techniques. Other penalty functions having other characteristics may be used.

Although not required, for functionality, in order to attain enhanced speed, beamlet optimizations can be conducted simultaneously (possibly running on a multiprocessor hardware system such as the PEREGRINE dose calculation engine) for a wide range of penalty function parameters, starting with those specified by the user, and spanning the space of possible treatment options. Coverage of this phase space can be accomplished by randomized selection methods, systematic parameter variation, or parameter variation guided by goal-targeted mechanisms such as multiobjective decision theory.

Referring to FIG. 1, dose distributions are assessed against specific criteria (16). Based on the set(s) of assessment criteria specified by the user, FALCON analyzes all beamlet optimization results, voxel-by-voxel, to determine a treatment plan that best meets each set of selection criteria. Several different types of assessment criteria can be used, based on concepts such as dose-volume analysis, in which dose to various parts of the body can be constrained, minimized, or maximized, and projected biological response, in which tumor control and tissue damage can be constrained, minimized, or maximized. Dose distributions are calculated in parallel for a range of target dose and desirability (how much the user wants that particular dose) maps. The resulting dose distributions are judged against multiple sets of assessment criteria. Based on the results of these assessments, FALCON either exits or continues to search the space of target dose and desirability, optimizing beamlet for each set, then judging the new results against the multiple sets of assessment criteria. Once the assessment phase is completed, a resulting optimized plan 18 is reported for each set of assessment criteria.

Figure 3:
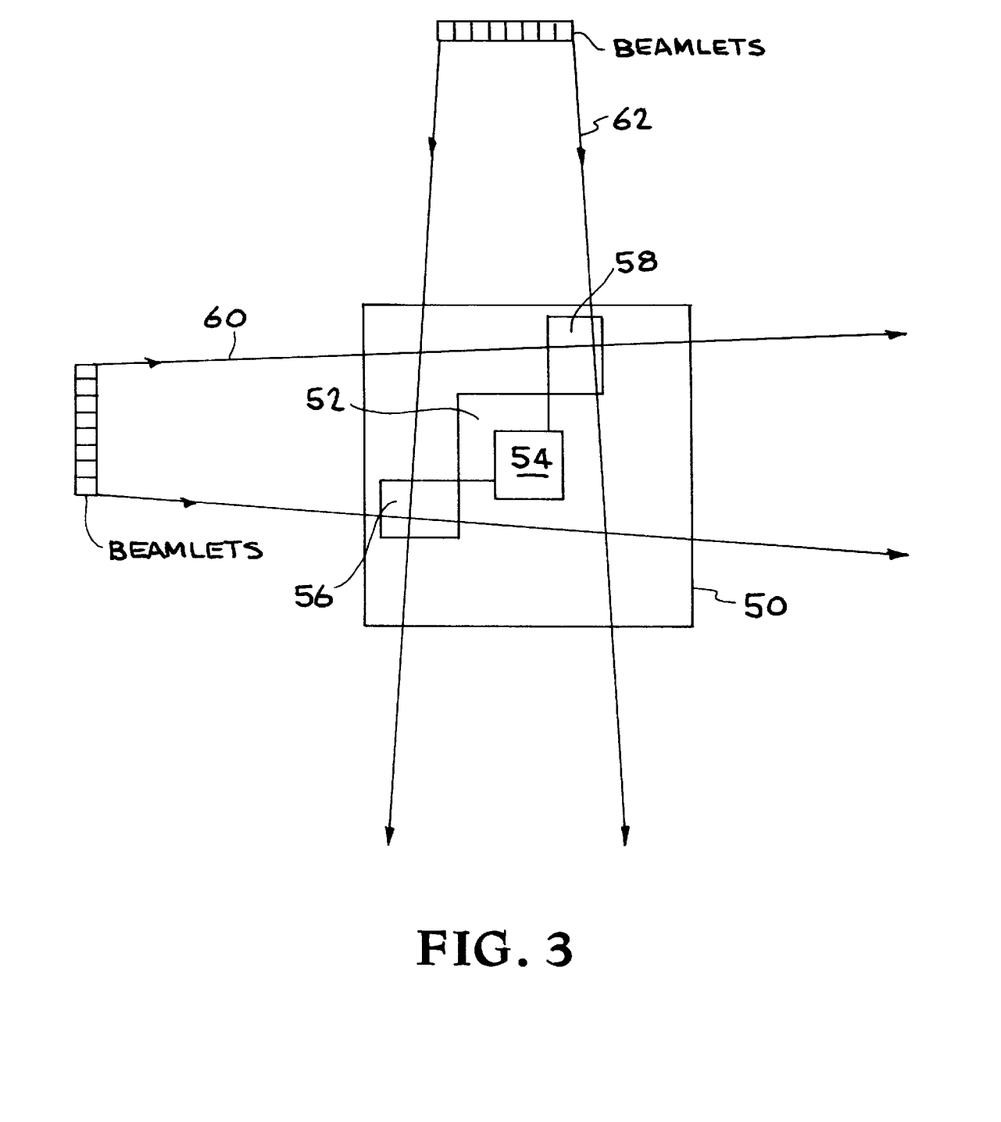
FIG. 3 is a description of the patient (in this case, a test phantom) and incident beam directions.

The following example, demonstrates the operation and usefulness of FALCON for automatic treatment planning. FIG. 3 illustrates a water box 50 with an L-shaped target volume 52, located next to a square air cavity 54 and surrounded by two sensitive structures 56 and 58. This problem was chosen because of its similarity to a larynx tumor configuration, with the tumor adjacent to an air cavity and because of the intrinsic difficulty of optimizing dose with adjacent heterogeneous target and sensitive structures. PEREGRINE dose calculations have shown the importance of accurate, Monte Carlo dose calculations and the need for intensity modulation to deliver a uniform dose distribution to areas with tissue heterogeneity.

The user has specified two incident beams 60 and 62, located 90 degrees apart. FIG. 3 illustrates the "CT scan" and user-specified beam directions. Assessment criteria are specified in Table 1, which shows a summary of four sets of assessment criteria to be used by FALCON to find the best treatment plan.

Once the "patient" description, input beam configuration and assessment criteria have been specified, FALCON begins the treatment planning process.

First, FALCON calculates the dose for each beamlet. For this case, FALCON relies on the highly accurate PEREGRINE dose calculation system, which uses first-principles physics to model the effects of the air heterogeneity in the beamlet dose distribution. The dose distribution for each unit-weight beamlet is individually calculated and stored before any optimization takes place. This means that the dose calculation is done once, and beamlet dose distributions can be reused repeatedly during the optimization process.

During the beamlet optimization phase, in this example, FALCON uses a quadratic penalty function to optimize beamlet intensities. In order to cover the space of practical dose delivery scenarios, FALCON varies the penalty function parameters (tumor dose, sensitive structure dose, and the "desirability" factor). For each set of penalty function parameters, FALCON optimizes beamlet intensities by superimposing the precalculated beamlet dose distributions voxel by voxel on the irradiated volume.

The optimized dose distributions determined with different penalty function parameters are then judged on the basis of the assessment criteria. Table 1 summarizes the assessment criteria specified for this problem. FIGS. 4A–D and 5A–B illustrate how different criteria sets result in different dose distributions.

Figure 4A:
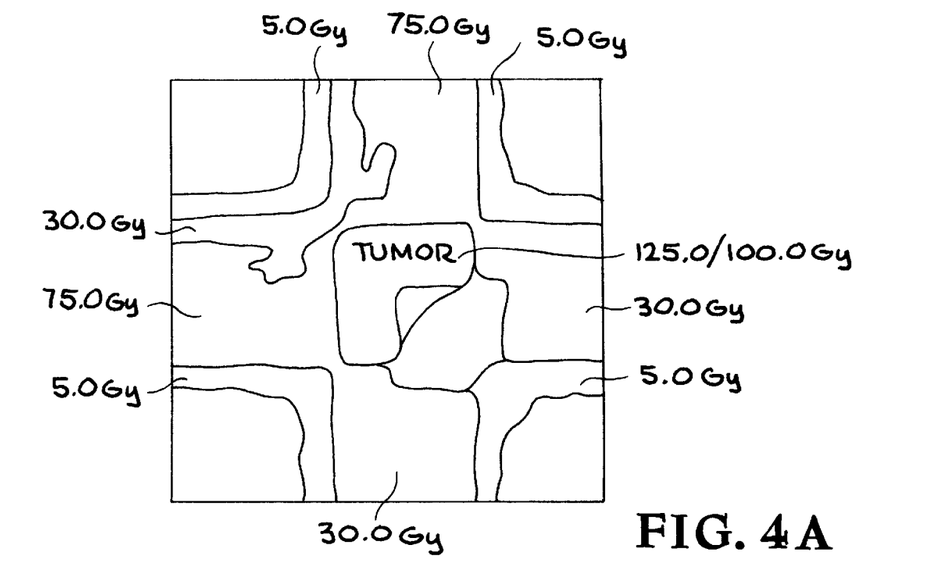
FIGS. 4A–4D show that dose distributions related to the four specified criteria sets clearly show that different assessment criteria results in different optimized plans.

Referring to FIG. 4A, for Criteria Set I, the planner forces the dose to the tumor to be >75 Gy, then tries to minimize the dose to the sensitive structures. This results in small parts of the sensitive structures receiving greater than their tolerance dose of 30 Gy. This planning strategy represents an aggressive approach that seeks first to cure the tumor, and accepts some potential complications. It may be the approach of choice if some damage to sensitive structures is tolerable, and/or there is a real chance of curing the patient's tumor.

Figure 4B:
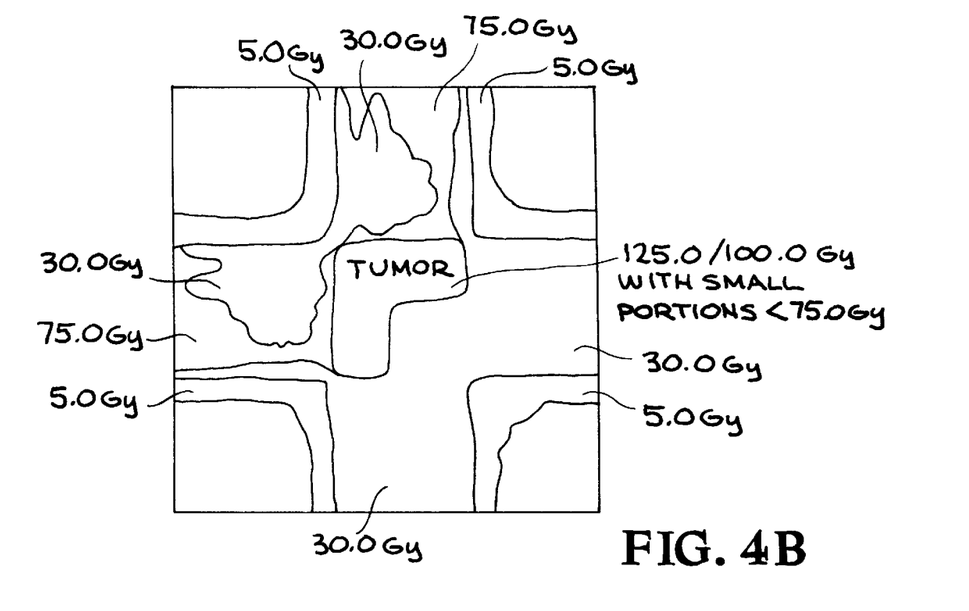
Figure 4C:
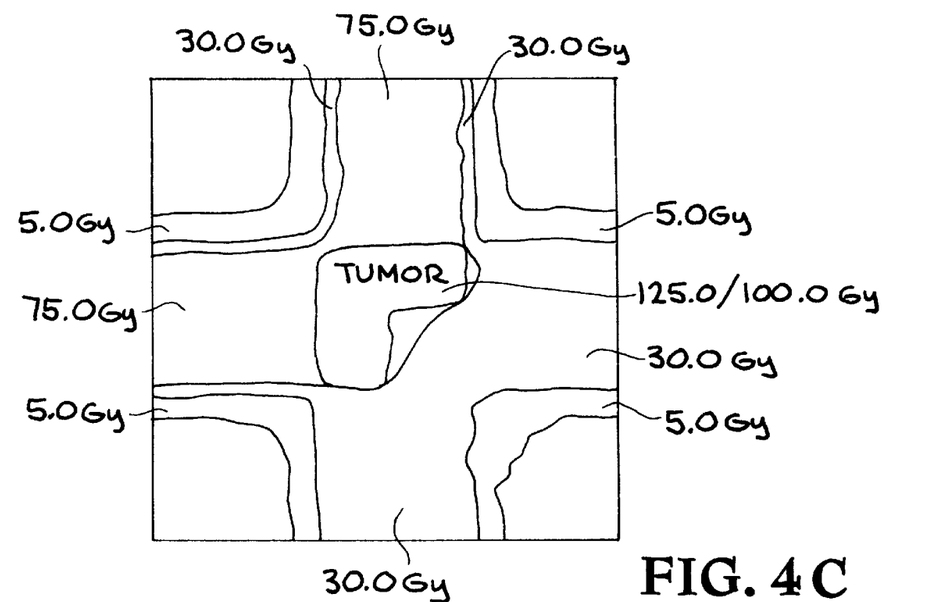
Figure 4D:
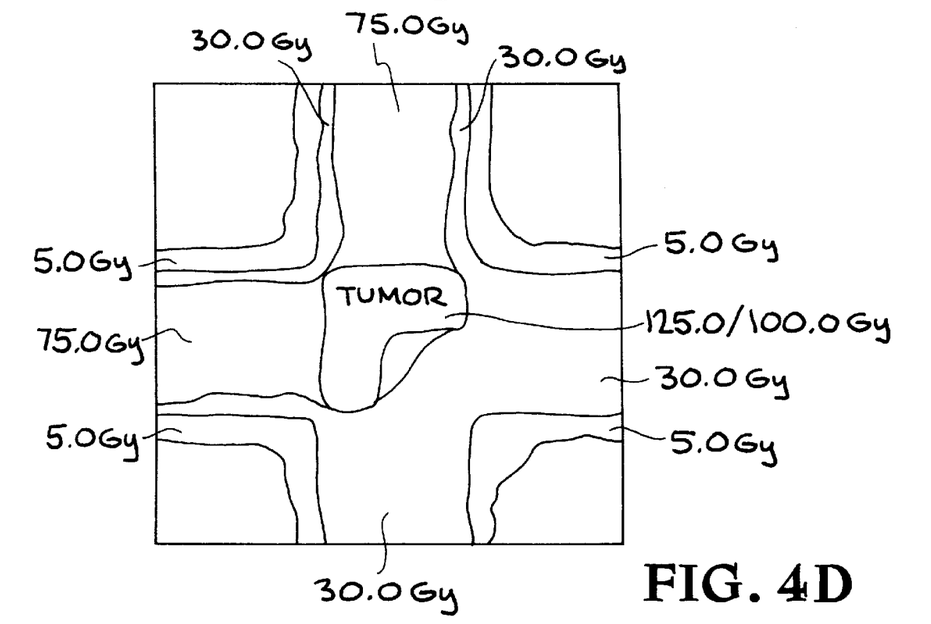
Figure 5A:
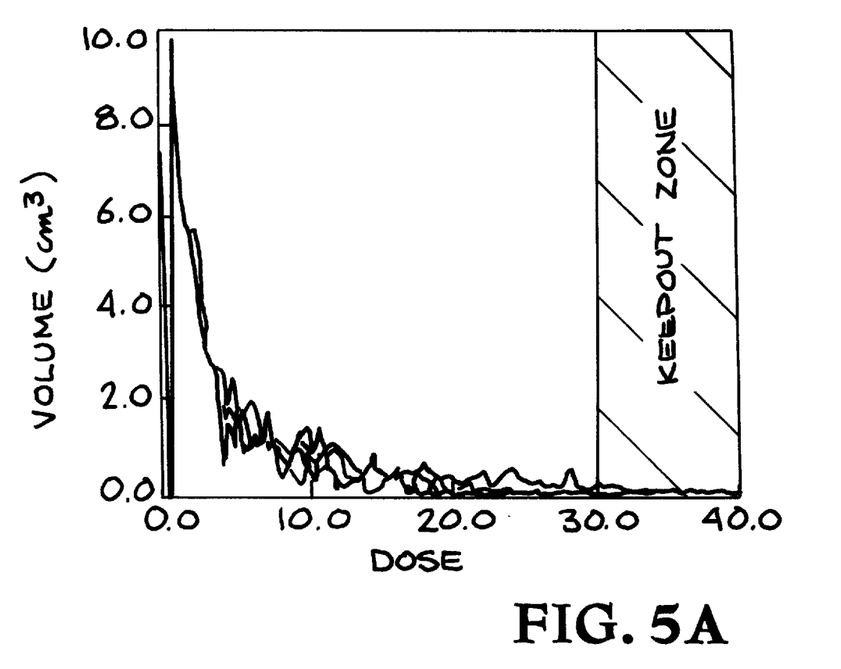
FIGS. 5A and 5B shows that dose volume histograms for the target and sensitive structure further illustrate the impact of different assessment criteria.
Figure 5B:
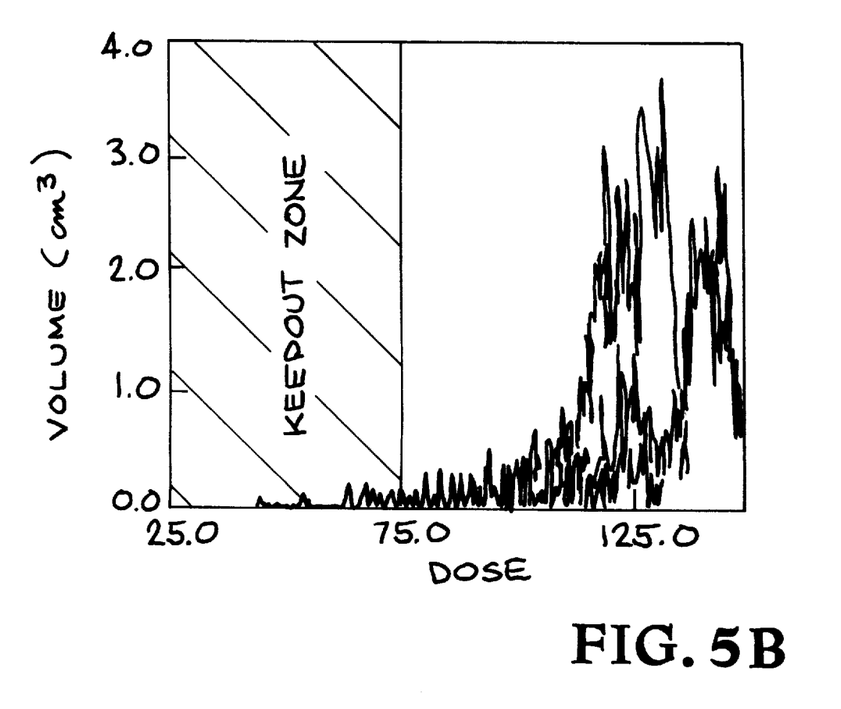

Criteria Set II shown in FIG. 4B represents a more conservative approach that might be used if damage to sensitive structures would cause severe damage or life-threatening conditions (e.g., transecting the spinal cord). This criteria set seeks first to keep the sensitive structure dose below its tolerance, then tries to maximize the tumor dose. It results in small parts of the tumor being treated with doses lower than the specified "curative" dose of 75 Gy.

Criteria Sets III and IV represent two strategies that explicitly attempt to maximize tumor control while minimizing sensitive structure damage. Criteria Set III, shown in FIG. 4C, accomplishes this through a dose-volume approach: it maximizes the difference between the volume of tumor receiving dose >75 Gy and the volume of sensitive structures receiving dose <30 Gy. Criteria Set IV, shown in FIG. 4D, accomplishes its objective by optimizing the difference between the probabilities of tumor control and normal tissue complications, as calculated from biological models which mathematically describe the σ-shaped organ (and tumor) response curves. Both of these explicit optimization criteria result in higher overall doses to the tumor, while keeping the overall dose to the sensitive structures approximately the same as Criteria Sets I and II. Very small concessions are made in that the about 2–4 mm³ dose volumes in the case where the tumor fall below the 75 Gy curative dose.

Figure 6:
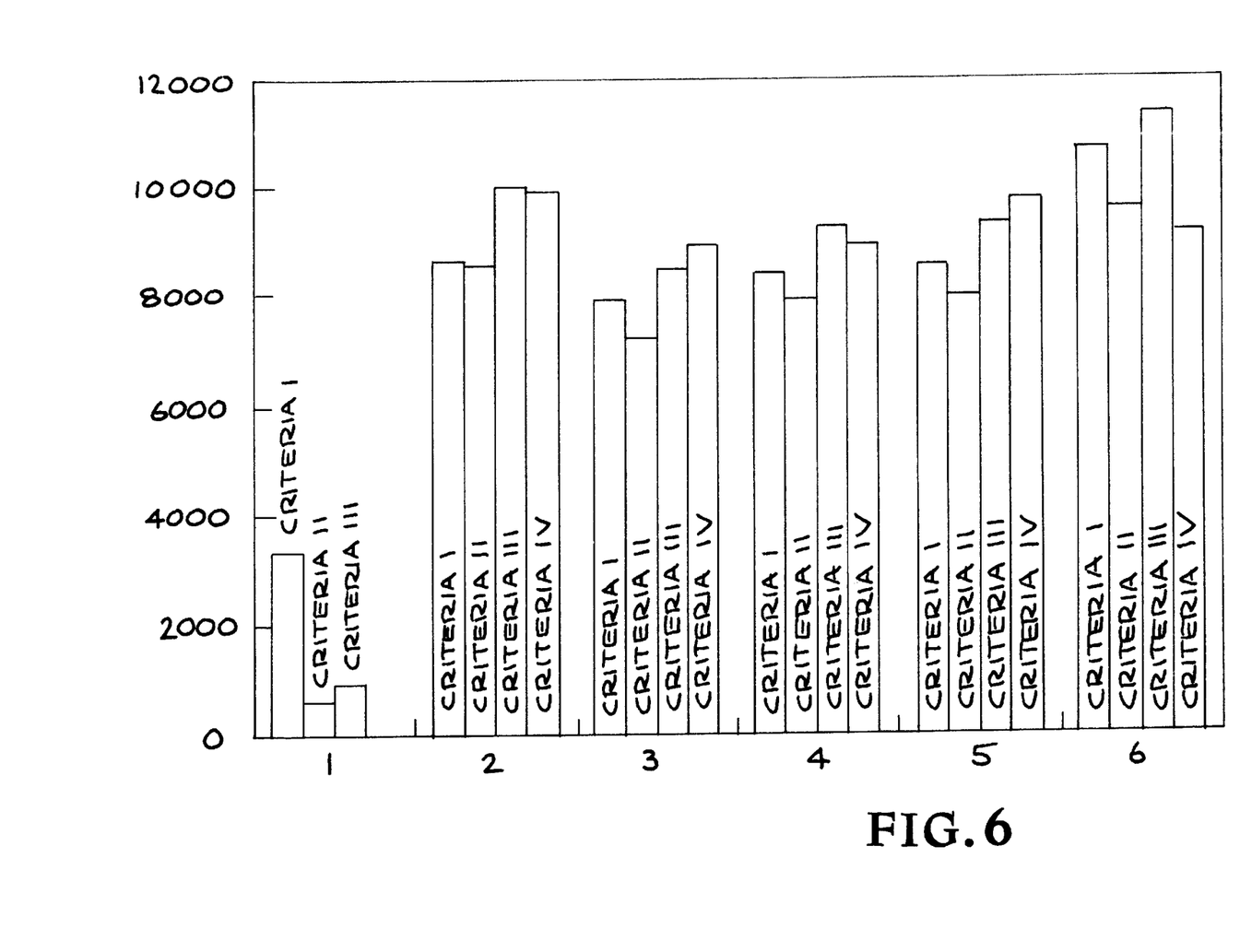
FIG. 6 shows beamlet intensities for one beam, determined for the treatment plans that best meet the four sets of selection criteria.

FIG. 6 shows the beamlet intensities that FALCON recommends, based on the four different sets of assessment criteria. Each beam was divided into ten beamlets. Four of the ten beamlets are zero in every case. Since the problem is symmetric, beamlet intensities are the same (actually, a mirror reflection) for each beam. The figure shows beamlet intensities for one beam, determined for the treatment plans that best meet the four sets of selection criteria.

The above example illustrates how FALCON works and how it facilitates rapid, automatic treatment planning for multiple assessment criteria. It is clear that relatively small differences in beamlet intensity patterns that would not have been anticipated using standard (non-optimized) treatment planning methods result in significantly different dose distributions, that represent optimization to various type of assessment criteria. Because radiation treatment planning is currently done primarily through physician experience, actual decision-making criteria for treatment planning are now not well-known. FALCON gives the physician the ability to rapidly determine highly-accurate treatment plans that best meet a variety of criteria sets. This allows the physician to explore the meaning of both explicit and hidden assumptions used in plan selection, and ultimately arrive at the best treatment plan for the patient. In time, with accumulated experience using FALCON, new treatment strategies will be developed that can provide even better patient outcomes.

FALCON provides a number of advantages, including the following. FALCON is the first treatment plan optimization system that allows the use of true three-dimensional Monte Carlo dose calculations for treatment planning. Unlike other systems, FALCON calculates beamlet dose distributions only once. This allows very rapid optimization with the highest accuracy, since doses from each beamlet do not need to be calculated for each iteration. It is the only treatment plan optimization system that divides optimization and assessment, allowing rapid, parallel variation of optimization parameters in order to reach a treatment plan that best matches each set of assessment criteria. FALCON supports numerous types of optimized treatment delivery methods, including Intensity Modulated Radiation Therapy (IMRT) delivered with blocks, fixed multileaf collimators, dynamic multileaf collimators, molded modifiers (compensators), mixed modalities (combinations of beam types) etc. These features make FALCON a significant advancement over currently-existing treatment planning systems. In addition, FALCON can be used for all types of radiation treatment planning modalities Changes and modifications in the specifically described embodiments can be carried out without departing from the scope of the invention, which is intended to be limited by the scope of the appended claims.

What is claimed is:

1. A method for automated radiation therapy dose planning, comprising:

providing patient description, bean description, a penalty function and assessment criteria;

dividing the radiation treatment beam into individual beamlets;

determining the dose distribution in the patient for each beamlet;

storing the absolute dose distribution per monitor intensity unit for each beamlet;

determining the intensity-weight of each beamlet by optimizing according to a penalty function; and analyzing all beamlet optimization results, voxel-by-voxel, or dosel by dosel to determine a treatment plan that best meets each set of assessment criteria, wherein the step of determining the dose distribution comprises:

constructing patient-dependent information necessary for a Monte-Carlo transport calculation, executing said Monte-Carlo transport calculation; and producing, from said patient-dependent information and said Monte-Carlo transport calculation, a 3-dimensional map of the dose delivered to said patient, wherein the step of constructing patient-dependent information comprises:

determining user-specified options from an input of (i) Monte Carlo parameters, (ii) physics options and (iii) output options, to set switches for code control;

determining the number of energy groups for transport of each particle type from nuclear/atomic/ electron data to provide the number of energy groups for each particle type;

using computed tomography (CT) information to define dimensions and material composition for each CT voxel from an input of (i) user options comprising user-specified thresholds for processing CT scans and (ii) a CT scan array to contribute to the production of a material specification array;

reading user input specifying each radiation beam source from an input of radiation source specifications comprising external beam characteristics and modifiers to provide radiation source angular and energy distributions and arrays describing beam delivery components;

completing the final setup for material arrays from an input of material composition data which is defined internally within the code to provide problem dependent material and isotope specification arrays;

reading nuclear and atomic data and constructing transport arrays from an input of (i) said nuclear/atomic/electron data, (ii) said number of energy groups for each particle type and (iii) said problem-dependent material and isotope specification arrays to provide (i) nuclear and atomic transport data arrays, (ii) heavy charged particle transport data arrays and (iii) energy group structure for each particle type; and reading electron data and constructing transport arrays from an input of (i) said nuclear/atomic/electron data and (ii) said problem-dependent material and isotope specification arrays to produce electron transport data arrays.

2. The method of claim 1, wherein the patient description includes a three-dimensional map that describes the patient's anatomy suitable for radiation dose calculations in the context of a particular treatment method.

3. The method of claim 1, wherein the patient description includes identification of tumor/sensitive structures.

4. The method of claim 1, wherein the beam description specifies the character (energy, particle type, delivery device) and orientation of each radiation beam.

5. The method of claim 1, wherein the penalty function is a mathematical function for optimization of beamlet intensities.

6. The method of claim 1, wherein the assessment criteria is selected from a group consisting of dose-volume analysis, tumor-dose maximization and biological response.

7. The method of claim 1, wherein said beamlets are arbitrarily shaped sub-beams that tile the treatment beam, and are defined by masks oriented perpendicular to the central ray of each beam.

8. The method of claim 1, wherein the penalty function comprises a quadratic, least-squares-type penalty function, P having the form:

$$P(a_1 \ldots a_n) = \int F \bullet [T-D]^2 \, dV$$

where F is the "desirability factor" (initialized to 1), T is the target dose, and D is the calculated dose, wherein D can also be expressed as the sum of the doses contributed by each beamlet, as in the formula: $D = \Sigma a_i D_i$, where $a_i$ is the beamlet amplitude and $D_i$ is the dose per unit amplitude of the ith beamlet, wherein F, T, and D are all functions of position in the volume.

9. The method of claim 1, wherein the assessment criteria includes dose-volume analysis, in which dose to various parts of the body can be constrained, minimized or maximized and wherein said assessment criteria further includes projected biological response, in which tumor control and tissue damage can be constrained, minimized or maximized.

10. The method of claim 1, wherein the assessment criteria includes four sets of criteria, wherein Criteria Set I forces the dose to the tumor to be >75 Gy, then tries to minimize the dose to the sensitive structures, wherein Criteria Set II seeks first to keep the sensitive structure dose below its tolerance, then tries to maximize the tumor dose, wherein Criteria Sets III and IV represent two strategies that explicitly attempt to maximize tumor control while minimizing sensitive structure damage, wherein Criteria Set III maximizes the difference between the volume of tumor receiving dose >75 Gy and the volume of sensitive structures receiving dose <30 Gy and wherein Criteria Set IV optimizes the difference between the probabilities of tumor control and normal tissue complications.

11. The method of claim 1, wherein the step of constructing patient dependent-information comprises:

optionally reading user-drawn contours that describe patient structures and modifying said material specification arrays from an input of a second set of user options comprising user-drawn contours, to complete the production of said material specification array and to provide a standard deviation zone identification array; and reading user input specifying each internal (brachytherapy) source, if any, from an input of an internal radiation source specification to provide radiation source angular and energy distributions.

12. A method for automated radiation therapy dose planning, comprising:

providing patient description, beam description, a penalty function and assessment criteria;

dividing the radiation treatment beam into individual beamlets;

determining the dose distribution in the patient for each beamlet;

storing the absolute dose distribution per monitor intensity unit for each beamlet;

determining the intensity-weight of each beamlet by optimizing according to a penalty function; and analyzing all beamlet optimization results, voxel-by-voxel, or dosel by dosel to determine a treatment plan that best meets each set of assessment criteria, wherein the step of determining the dose distribution comprises:

constructing patient-dependent information necessary for a Monte-Carlo transport calculation;

executing said Monte-Carlo transport calculation; and producing, from said patient-dependent information and said Monte-Carlo transport calculation, a 3-dimensional map of the dose delivered to said patient, wherein the step of executing the Monte Carlo transport calculation comprises:

selecting particle attributes for a primary particle arising from an external radiation beam from an input of (i) radiation source angular and energy distributions, (ii) arrays describing beam delivery components, (iii) material data, (iv) nuclear and atomic transport data arrays and (v) number and energy group structure for each particle type, and to contribute a first portion to the provision of attributes of one particle, wherein said attributes comprise energy, location, direction and type;

optionally selecting particle attributes for a primary particle arising from an internal radiation source, if any, from an input of radiation source angular and energy distributions to contribute a second portion to the provision of said attributes of one particle;

selecting a particle that has been created by an interaction of another particle in a transport mesh from an input of secondary particle arrays to provide a third portion to and complete the provision of said attributes of one particle;

(i) optionally tracing a neutron through said transport mesh, (ii) recording energy deposited by said neutron and (iii) storing attributes of secondary particles produced in a secondary particle array from an input of (i) attributes of one particle (said neutron), (ii) switches set for code control, (iii) a material specification array, (iv) material data (v) nuclear transport data arrays, and (vi) the number and energy group structure for said neutrons, to provide secondary particle arrays for neutrons and a 3-D energy deposit map for neutrons;

(i) tracking a photon through said transport mesh, (ii) recording energy deposited by said photon and (iii) storing attributes of secondary particles produced in secondary particle arrays for photons from an input of (i) attributes of one photon particle, (ii) said switches set for code control, (iii) said material specification arrays, (iv) said material data, (v) said atomic transport data arrays, and (vi) number and energy group structure for photons, to provide secondary particle arrays for photons and a 3-D energy deposit map for photons;

(i) optionally tracking a heavy charged particle through said transport mesh, (ii) recording the energy deposited by said heavy charged particle and (iii) storing the attributes of secondary particles produced in secondary particle arrays for heavy charged particles from an input of (i) said switch settings for code control, (ii) said material specification array, (iii) said material data, (iv) said nuclear transport data arrays, (v) heavy charged particle transport data arrays and (vi) the number and energy group structure for heavy charged particles to provide secondary particle arrays for heavy charged particles and a 3-D deposit map for heavy charged particles;

(i) optionally tracking a primary electron through said transport mesh, (ii) recording the energy deposited by said electron and (iii) storing the attributes of secondary particles produced in secondary particle arrays for primary electrons from an input of (i) the attributes of one particle (primary electron), (ii) said switch settings for code control, (iii) said material specification array, (iv) said material data, (v) electron transport data arrays and (vi) said number and energy group structure for said electrons to provide secondary particle arrays for primary electrons and a 3-D energy deposit map for primary electrons;

(i) optionally tracking secondary electrons through said transport mesh, (ii) recording the energy deposited by said secondary electron and (iii) storing the attributes of secondary particles produced (secondary electrons) in secondary particle arrays for secondary electrons from an input of (i) the attributes of one particle (a secondary electron), (ii) said switch settings for code control, (iii) said material specification array, (iv) said material data, (v) said electron transport data arrays and (vi) said number and energy group structure for electrons to provide said secondary particle arrays for secondary electrons and a 3-D energy deposit map for secondary electrons;

adding all 3-D energy deposit maps calculated over a batch to a 3-D energy deposit map for the problem from an input of a 3-D energy deposit map calculated for a single batch to provide an integral 3-D energy deposit map;

updating the arrays necessary for a standard deviation calculation with energy deposit information determined from each said batch from an input of said integral 3-D energy deposit map and a standard deviation zone ID array to provide standard deviation precalculation arrays; and calculating standard deviation from an input of said standard deviation precalculation arrays to provide standard deviation arrays.

13. The method of claim 12, wherein the step of producing said patient dependent information and said Monte Carlo transport calculation, a 3-dimensional map of the dose delivered to said patient, comprises:

writing a problem summary into an ASCII output file;

calculating the dose from said integral 3-D map of energy deposited; and writing out a 3-D dose map from an input of said integral 3-D energy deposit array and said standard deviation arrays, wherein said 3-D dose map is written in a form selected from a group consisting of ASCII and binary.

14. The method of claim 12, wherein said radiation therapy dose planning comprises a radiation source that produces particles selected from a group consisting of photons, light charged particles (electrons, positrons), heavy charged particles (protons, deuterons, tritons, helium-3, alpha particles), and neutrons.

15. The method of claim 12, wherein said radiation therapy dose planning comprises at least one external radiation source delivery system.

16. The method of claim 12, wherein said radiation therapy dose planning comprises at least one internal radiation source delivery system.

17. The method of claim 12, wherein said radiation therapy dose planning comprises a source delivery system selected from a group consisting of teletherapy, brachytherapy and boron neutron capture therapy (BNCT).

* * * * *